United States Patent
Hartingh et al.

(10) Patent No.: US 11,958,864 B2
(45) Date of Patent: Apr. 16, 2024

(54) TETRACYCLIC HETEROCYCLE COMPOUNDS USEFUL AS HIV INTEGRASE INHIBITORS

(71) Applicant: Merck Sharp & Dohme LLC, Rahway, NJ (US)

(72) Inventors: Timothy John Hartingh, Richlandtown, PA (US); John A. McCauley, Maple Glen, PA (US); Tao Yu, Edison, NJ (US); Yonglian Zhang, East Brunswick, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/670,689

(22) Filed: Feb. 14, 2022

(65) Prior Publication Data

US 2022/0259227 A1   Aug. 18, 2022

Related U.S. Application Data

(60) Provisional application No. 63/149,927, filed on Feb. 16, 2021.

(51) Int. Cl.
*C07D 498/22* (2006.01)
*A61K 45/06* (2006.01)

(52) U.S. Cl.
CPC ............ *C07D 498/22* (2013.01); *A61K 45/06* (2013.01)

(58) Field of Classification Search
CPC .......................... C07D 498/22; A61K 31/5365
USPC .......................................... 544/95; 514/229.5
See application file for complete search history.

(56) References Cited

FOREIGN PATENT DOCUMENTS

WO   2018102485 A1   6/2018

OTHER PUBLICATIONS

Pearl, L.H., et al.,, "A Structural Model For The Retroviral Proteases", Nature, 1987, pp. 351-354, vol. 329.
Power, M.D., et al.,, "Nucleotide Sequence of SRV-1, a Type D Simian", Science, 1986, pp. 1567-1572, vol. 231.
Ratner, L., et al.,, "Complete Nucleotide Sequence Of AIDS Virus, HTLV-III", Nature, 1985, pp. 277-284, vol. 313.
Toh, H., et al.,, "Lose Structural Resemblance Between Putative Polymerase Of A *Drosophila* Transposable Genetic Element 17.5 and Pol Gene Product of Moloney Murine Leukaemia Virus", The EMBO Journal, 1985, pp. 1267-1272, vol. 4, No. 5.

*Primary Examiner* — Jeffrey H Murray
(74) *Attorney, Agent, or Firm* — Eric Greenwald; John C. Todaro

(57) ABSTRACT

The present invention relates to Tetracyclic Heterocycle Compounds of Formula (I):

and pharmaceutically acceptable salts or prodrug thereof, wherein $R^1$ is as defined herein. The present invention also relates to compositions comprising at least one Tetracyclic Heterocycle Compound, and methods of using the Tetracyclic Heterocycle Compounds for treating or preventing HIV infection in a subject.

19 Claims, No Drawings

TETRACYCLIC HETEROCYCLE COMPOUNDS USEFUL AS HIV INTEGRASE INHIBITORS

FIELD OF THE INVENTION

The present invention relates to Tetracyclic Heterocycle Compounds, compositions comprising at least one Tetracyclic Heterocycle Compound, and methods of using the Tetracyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA, and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

SUMMARY OF THE INVENTION

In one aspect, the present invention provides Compounds of Formula (I):

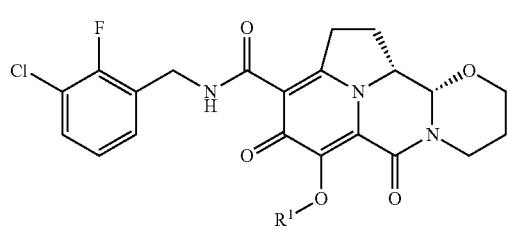

(I)

or a pharmaceutically acceptable salt thereof, wherein:
$R^1$ is $CHR^2$—O—C(O)—Y—$R^3$, C(O)—$C_1$-$C_{10}$ alkyl, $CHR^2$—O—P(O)(OH)$_2$ or

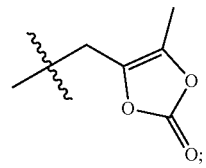 [SMILES: *Cc1oc(=O)oc1C]

Y is a bond or —O—;
$R^2$ is hydrogen or $C_1$-$C_6$ alkyl;
$R^3$ is selected from the group consisting of $C_1$-$C_6$ alkyl, $(CH_2)_x$—O—$C_1$-$C_6$ alkyl, and $(CH_2)_x$—$NR^4R^5$, wherein said $C_1$-$C_6$ alkyl group can be optionally substituted with one to three groups independently selected from the group consisting of halo, hydroxy, methoxy and ethoxy;
$R^4$ is hydrogen or $C_1$-$C_6$ alkyl;
$R^5$ is hydrogen or $C_1$-$C_6$ alkyl;
x is an integer from one to four.

The Compounds of Formula (I) (also referred to herein as the "Tetracyclic Heterocycle Compounds") and pharmaceutically acceptable salts or prodrugs thereof may be useful, for example, for inhibiting HIV viral replication or replicon activity, or for treating or preventing HIV infection in a subject. Without being bound by any specific theory, it is believed that the Tetracyclic Heterocycle Compounds inhibit HIV viral replication by inhibiting HIV Integrase.

Accordingly, the present invention provides methods for treating or preventing HIV infection in a subject, comprising administering to the subject an effective amount of at least one Tetracyclic Heterocycle Compound of formula I, or pharmaceutically acceptable salts thereof.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Tetracyclic Heterocycle Compounds, compositions comprising at least one Tetracyclic Heterocycle Compound, and methods of using the Tetracyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tetracyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prophylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 10 carbon atoms ($C_1$-$C_{10}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "halo," as used herein, means —F, —Cl, —Br or —I.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

The compounds of the instant invention are prodrugs of (11aS,11bR)-N-(3-chloro-2-fluorobenzyl)-5-hydroxy-4,6-dioxo-1,2,4,6,9,10,11a,11b-octahydro-8H-[1,3]oxazino[2',3':3,4]pyrazino[2,1,6-cd]indolizine-3-carboxamide, which is also referred to as Compound A, and has the following chemical structure:

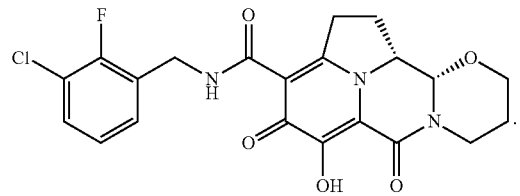 [SMILES: O=C(NCc1cccc(Cl)c1F)c1c2n3c(c(O)c1=O)C(=O)N1CCCO[C@H]1[C@H]3CC2]

Synthesis of and the ability of (11aS,11bR)-N-(3-chloro-2-fluorobenzyl)-5-hydroxy-4,6-dioxo-1,2,4,6,9,10,11a,11b-octahydro-8H-[1,3]oxazino[2',3':3,4]pyrazino[2,1,6-cd]indolizine-3-carboxamide to inhibit HIV integrase are described in PCT International Application WO2018/102485, published on Jun. 7, 2018 to Merck Sharp & Dohme Corp., which is hereby incorporated by reference in its entirety.

The term "prodrug" means a compound (e.g., a drug precursor) that is transformed in vivo to provide a pharmacologically active compound or a pharmaceutically acceptable salt of the compound. The transformation may occur by various mechanisms (e.g., by metabolic or chemical processes), such as, for example, through hydrolysis in blood.

Solvates of the compounds of the invention are also contemplated herein.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain situations, the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tetracyclic Heterocycle Compounds can form salts which are also within the scope of this invention. Reference to a Tetracyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tetracyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tetracyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tetracyclic Heterocycle Compounds may be atropisomers (e.g., substituted biaryls) and are considered as part of this invention. Enantiomers can also be directly separated using chiral chromatographic techniques.

It is also possible that the Tetracyclic Heterocycle Compounds may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tetracyclic Heterocycle Compound incorporates a double bond or a fused ring, both the cis- and trans-forms, as well as mixtures, are embraced within the scope of the invention.

When a subsituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

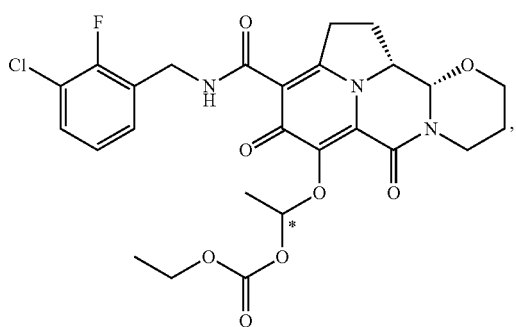 [SMILES: CCOC(=O)OC(C)Oc1c2n3c(c(C(=O)NCc4cccc(Cl)c4F)c1=O)CC[C@@H]3[C@@H]1OCCCN1C2=O]

is understood to encompass both stereoisomers at the indicated chiral center, the structures of which are as follows:

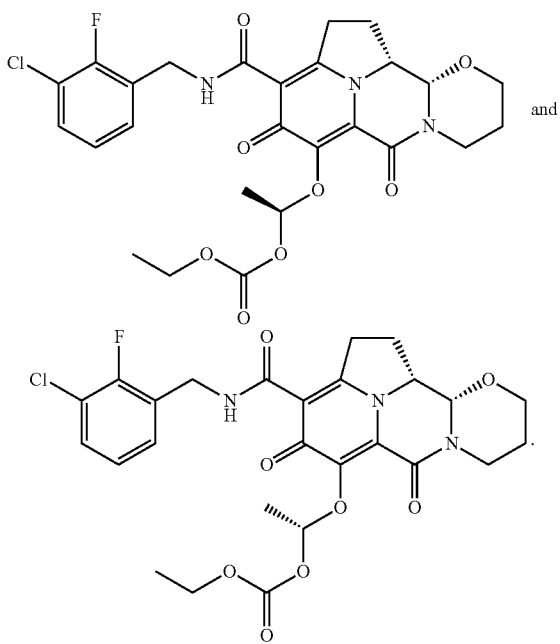

The N—C bond in the "right-side" fused ring

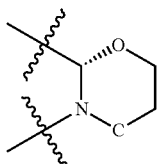 [SMILES: *[C@@H]1OCCCN1*]

of the compounds of Formula (I) can exist in any viable orientation.

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" and the like, is intended to apply equally to the salt and solvate of enantiomers, stereoisomers, rotamers, tautomers or racemates of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Tetracyclic Heterocycle Compounds may be useful in human and veterinary medicine for treating or preventing HIV infection in a subject. In one embodiment, the Tetracyclic Heterocycle Compounds can be inhibitors of HIV viral replication. In a specific embodiment, the Tetracyclic Heterocycle Compounds are inhibitors of HIV-1. Accordingly, the Tetracyclic Heterocycle Compounds may be useful for treating HIV infections and AIDS. In accordance with the invention, the Tetracyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Tetracyclic Heterocycle Compound or a pharmaceutically acceptable salt thereof. In a specific embodiment, the present invention provides methods for treating AIDS in a subject comprising administering to the subject an effective amount of at least one Tetracyclic Heterocycle Compound or a pharmaceutically acceptable salt thereof.

The Compounds of Formula (I)

The present invention provides Tetracyclic Heterocycle Compounds of Formula (I):

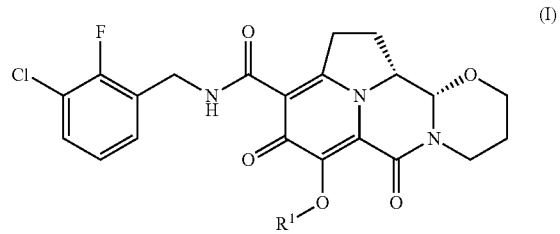

or a pharmaceutically acceptable salt thereof, wherein:
R$^1$ is CHR$^2$—O—C(O)—Y—R$^3$, C(O)—C$_1$-C$_{10}$ alkyl, CHR$^2$—O—P(O)(OH)$_2$ or

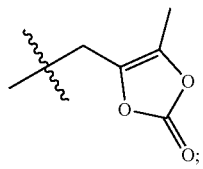

Y is a bond or —O—;
R$^2$ is hydrogen or C$_1$-C$_6$ alkyl;
R$^3$ is selected from the group consisting of C$_1$-C$_6$ alkyl, (CH$_2$)$_x$—O—C$_1$-C$_6$ alkyl, and (CH$_2$)$_x$—NR$^4$R$^5$, wherein said C$_1$-C$_6$ alkyl group can be optionally substituted with one to three groups independently selected from the group consisting of halo, hydroxy, methoxy and ethoxy;
R$^4$ is hydrogen or C$_1$-C$_6$ alkyl;
R$^5$ is hydrogen or C$_1$-C$_6$ alkyl;
x is an integer from one to four.

In an embodiment of the invention, R$^1$ is CHR$^2$—O—C(O)—Y—R$^3$. In another embodiment of the invention, R$^1$ is C(O)—C$_1$-C$_{10}$ alkyl. In another embodiment of the invention, R$^1$ is CHR$^2$—O—P(O)(OH)$_2$. In another embodiment of the invention, R$^1$ is

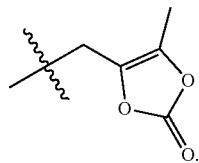 [SMILES: *Cc1oc(=O)oc1C]

In a class of the embodiment, R$^1$ is selected from:

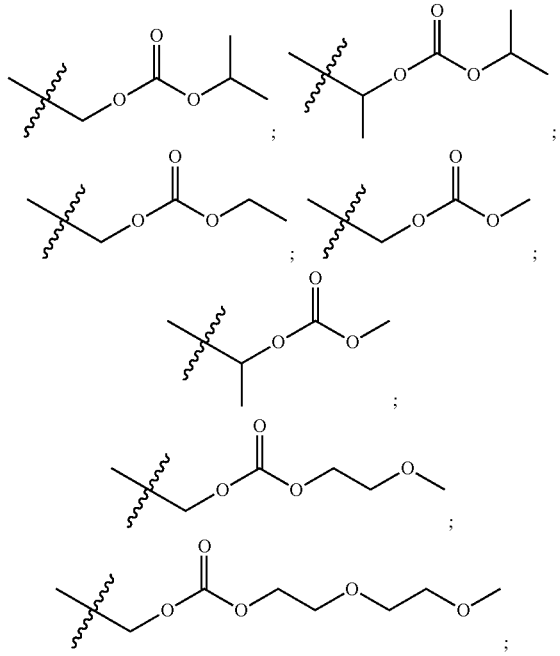

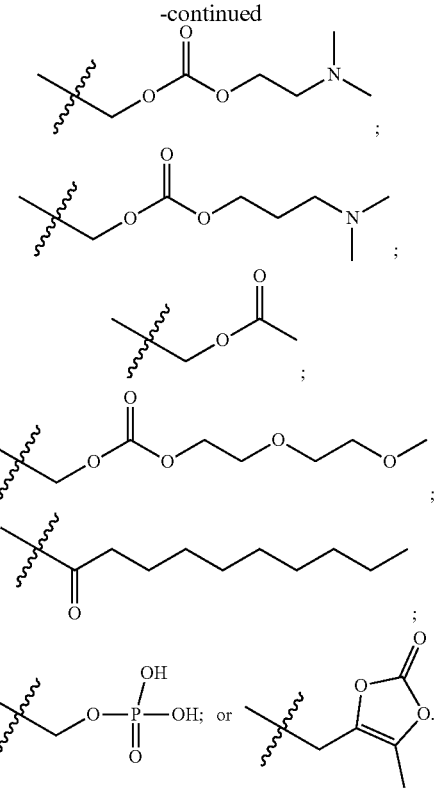

In a subclass of the embodiment, R$^1$ is

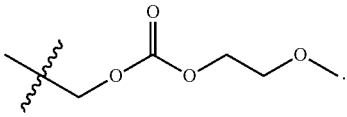 [SMILES: *COC(=O)OCCOC]

In an embodiment of the invention, R$^2$ is hydrogen or methyl. In a class of the embodiment, R$^2$ is hydrogen. In another class of the embodiment, R$^2$ is methyl.

In an embodiment of the invention, R$^3$ is C$_1$-C$_6$ alkyl, which is optionally substituted with one to three groups independently selected from the group consisting of halo, hydroxy, methoxy and ethoxy. In another embodiment of the invention, R$^3$ is (CH$_2$)$_x$—O—C$_1$-C$_6$ alkyl. In another embodiment of the invention, R$^3$ is (CH$_2$)$_x$—NR$^4$R$^5$.

In an embodiment of the invention, R$^4$ is methyl.
In an embodiment of the invention, R$^5$ is methyl.
In an embodiment of the invention, Y is —O—. In another embodiment of the invention, Y is a bond.

In an embodiment of the invention, x is one. In another embodiment of the invention, x is two. In another embodiment of the invention, x is three. In another embodiment of the invention, x is four.

In another embodiment, the Compounds of Formula (I) are in substantially purified form.

It is to be understood that any of the aforementioned embodiments may be combined with one or more separate embodiments.

Other embodiments of the present invention include the following:
(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HIV antiviral agents, immunomodulators, and anti-infective agents.

(n) The pharmaceutical composition of (m), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(o) A pharmaceutical combination that is (i) a pharmaceutically acceptable salt of a Compound of Formula (I) and (ii) a second therapeutic agent selected from the group consisting of HIV antiviral agents, immunomodulators, and anti-infective agents; wherein the pharmaceutically acceptable salt of the Compound of Formula (I) and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(q) A method of inhibiting HIV replication in a subject in need thereof which comprises administering to the subject an effective amount of a pharmaceutically acceptable salt of a Compound of Formula (I).

(r) A method of treating HIV infection and/or reducing the likelihood or severity of symptoms of HIV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(z) A pharmaceutical combination that is (i) a Compound of Formula (I) and (ii) or a pharmaceutically acceptable salt thereof, a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula (I) or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula (I) or a pharmaceutically acceptable salt thereof.

(dd) The method of (cc), wherein the Compound of Formula (I) or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV NRTIs (nucleoside reverse transcriptase inhibitors) and HIV NNRTIs (non-nucleoside reverse transcriptase inhibitors).

(ff) A method of inhibiting HIV replication in a subject in need thereof which comprises administering to the subject the pharmaceutical composition of (w), (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use (i) in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula (I) include compounds 1-8 as set forth in the Examples below, and pharmaceutically acceptable salts thereof.

Methods For Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in the Schemes below. Alternative synthetic pathways and analogous structures will be apparent to those skilled in the art of organic synthesis.

Abbreviations and acronyms employed herein include the following:

| | | | |
|---|---|---|---|
| Ac | Acetyl | Me | methyl |
| aq | Aqueous | MeCN | acetonitrile |
| AUC | Area under the curve | MeOH | methanol |
| Bu | Butyl | mg | milligrams |
| Bz | Benzoyl | MHz | megahertz |
| DCM | dichloromethane | min | minute |
| DHP | 3,4-dihydro-2H-pyran | μL | microliters |
| DIEA or Hünig's base | N,N-diisopropylethylamine | mL | milliliters |
| DMAP | 4-Dimethylaminopyridine | mmol | millimoles |
| DMF | dimethylformamide | MS | mass spectrometry |
| DMSO | dimethyl sulfoxide | NaI | sodium iodide |
| Et | Ethyl | NMR | nuclear magnetic resonance spectroscopy |
| EtOH | Ethanol | Ph | phenyl |
| EtOAc | ethyl acetate | P.O. | oral |
| g | Grams | PTSA | para-toluenesulfonic acid |
| GI | gastrointenstinal | Pr | propyl |
| h | Hour | RP | reverse phase |
| HCl | hydrochloric acid | RT or rt | room temperature (ambient, about 25° C.) |
| HIV | human immunodeficiency virus | sat or sat'd | saturated |
| HPLC | high-performance liquid chromatography | SFC | supercritical fluid chromatographyb |
| Hz | hertz | tBu | tert-butyl |
| IPA | isopropanol | TEA | triethylamine (Et$_3$N) |
| IV | intravenous | TEMED | tetramethylethylenediamine |
| iPr | isopropyl | TFA | trifluoroacetic acid |
| K$_2$CO$_3$ | potassium carbonate | THF | tetrahydrofuran |
| KI | Potassium iodide | TMS | tetramethylsilane |
| L | liter | UPLC | ultrahigh pressure liquid chromatography |
| LC | liquid chromatography | UV | ultraviolet |
| LC/MS | liquid chromatography mass spectrometry | UV/VIS | ultraviolet/visible |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Typically the analytical LC-MS system used consisted of a Waters ZQ™ platform with electrospray ionization in positive ion detection mode with an Waters Acquity™ Ultra Performance LC with autosampler. The column was commonly a Waters Acquity UPLC® BEH C18 1.0—50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a non-mass guided system. Usually they were performed on a Teledyne ISCO ACCQPrep HP150 UV system configured with ELSD, Collection Triggered by UV (254 and 215 NM) and ELSD, and a XBridge™ C-18 5 micron OBD™, 30 mm (id)×250 mm column. The mobile phases consisted of mixtures of acetonitrile (10-100%) in water containing 0.1% TFA. Flow rates were maintained at 50 mL/min, the injection volume ranged from was 1500-8000 μL, and the UV detection range was 210-400 nm. Mobile phase gradients were optimized for the individual compounds. Flash chromatography was usually performed using an ISCO CombiFlash® Rf apparatus or an ISCO CombiFlash® Companion XL on silica gel (32-63 μM, 60 Å pore size) in pre-packed RediSep® High Performance Gold cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz).

Several methods for preparing the compounds of this invention are also described in the Examples. Starting materials and intermediates were purchased commercially from common catalog sources or were made using known procedures, or as otherwise illustrated.

Preparation of Intermediate

INTERMEDIATE A

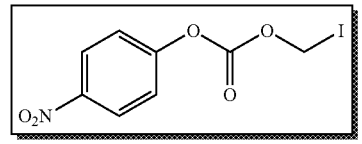

Step 1 iodomethyl (4-nitrophenyl) carbonate (INTERMEDIATE A)

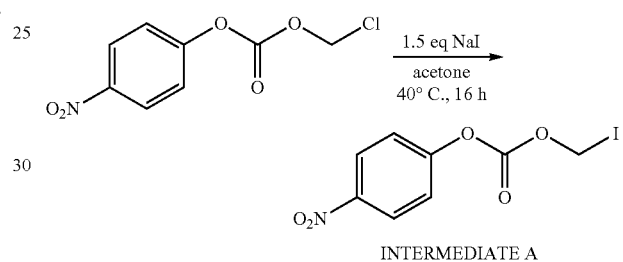

INTERMEDIATE A

To a solution of chloromethyl (4-nitrophenyl) carbonate (10.0 g, 43.2 mmol) in acetone (43.2 mL) was added sodium iodide (9.7 g, 64.8 mmol) at 25° C. The solution was stirred at 40° C. overnight. The reaction mixture was cooled to RT and then filtered. The filtrate was concentrated. The residue was dissolved in EtOAc (150 mL) and washed with a saturated solution of sodium thiosulfate (50 mL). The organic layer was then washed with brine (30 mL), dried (MgSO$_4$), filtered and concentrated to afford iodomethyl (4-nitrophenyl) carbonate (INTERMEDIATE A). This material was carried forward without purification.

Preparation of Examples

EXAMPLE 1

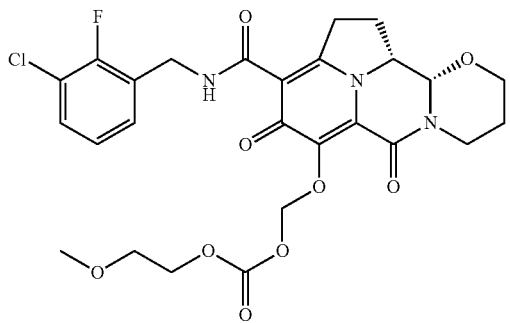

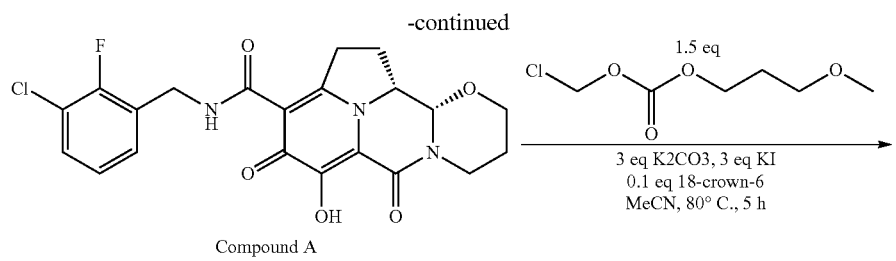
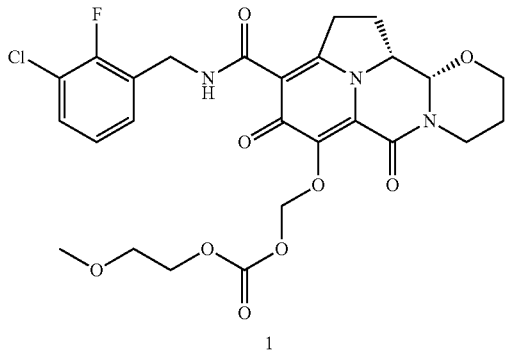

(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (2-methoxyethyl) carbonate

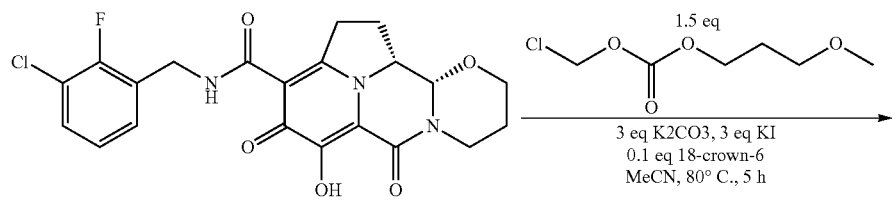
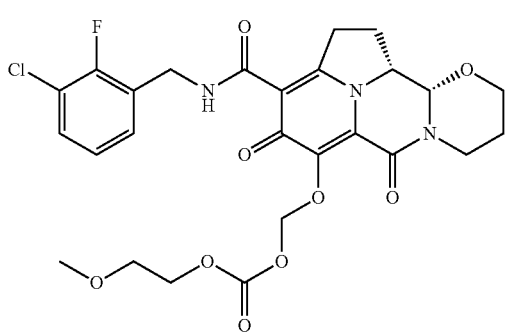

To a mixture of (11aS,11bR)-N-(3-chloro-2-fluorobenzyl)-5-hydroxy-4,6-dioxo-1,2,4,6,9,10,11a,11b-octahydro-8H-[1,3]oxazino[2',3':3,4]pyrazino[2,1,6-cd]indolizine-3-carboxamide (Compound A) (10.0 g, 22.33 mmol) and chloromethyl 2-methoxyethyl carbonate (5.65 g, 33.5 mmol) in acetonitrile (112 mL) was added potassium carbonate (9.26 g, 67 mmol), potassium iodide (11.12 g, 67 mmol), and 18-crown-6 (1,4,7,10,13,16-hexaoxacyclooctadecane) (0.59 g, 2.23 mmol). The resulting mixture stirred at 80° C. until reaction judged complete by LCMS (5 hours). The reaction mixture was cooled to ambient temperature, diluted with DCM (200 mL) and MeCN (100 mL) and stirred at the same temperature for 20 minutes. The mixture was filtered washing with DCM (200 mL), and the filtrate was concentrated. The residue was taken back up in DCM (500 mL) and filtered. The filtrate was purified directly by flash chromatography (330 g RediSep Rf Gold; 0-10% MeOH in DCM in 60 minutes; filtrate (DCM) loaded via pump for CombiFlash Companion XL system and then gradient run on CombiFlash Rf system) and pure fractions were concentrated to afford (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy) methyl (2-methoxyethyl) carbonate (Example 1). The material was then crystallized from 100% IPA. 1H NMR (500 MHz, Chloroform-d) δ 10.82 (t, J=5.8 Hz, 1H), 7.28 (t, J=9.0 Hz, 4H), 7.02 (td, J=7.9, 0.8 Hz, 1H), 5.91-5.84 (m, 2H), 4.95 (d, J=3.3 Hz, 1H), 4.79 (dd, J=13.2, 4.7 Hz, 1H), 4.65 (qd, J=15.5, 5.9 Hz, 2H), 4.48 (ddd, J=10.8, 6.9, 3.3 Hz, 1H), 4.39-4.27 (m, 2H), 4.22 (dd, J=11.6, 4.8 Hz, 1H), 4.13 (dd, J=19.2, 8.9 Hz, 1H), 3.93 (td, J=12.4, 2.5 Hz, 1H), 3.69-3.58 (m, 2H), 3.36 (s, 3H), 3.31-3.41 (m, 1H), 3.10 (td, J=12.9, 2.9 Hz, 1H), 2.46-2.25 (m, 2H), 2.04 m, 1H), 1.54 (d, J=13.9 Hz, 1H). LRMS (M+H)+: 580.3.
EXAMPLE 2
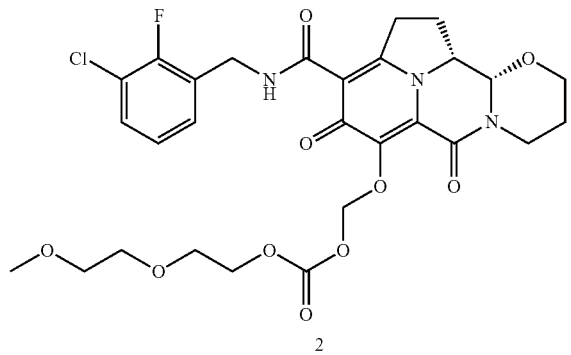
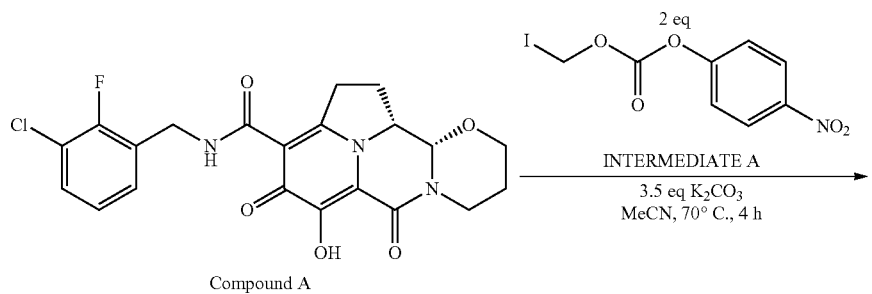
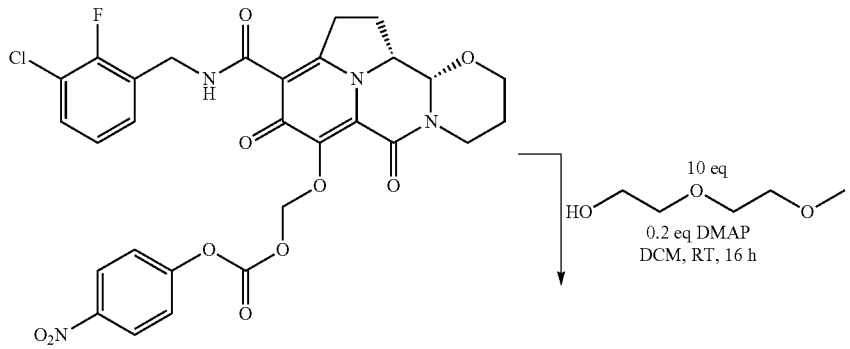
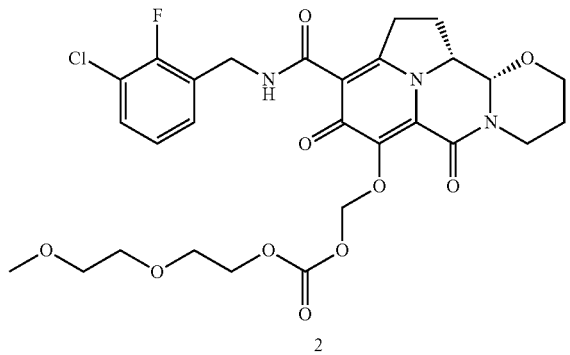

Step 1

(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (4-nitrophenyl) carbonate

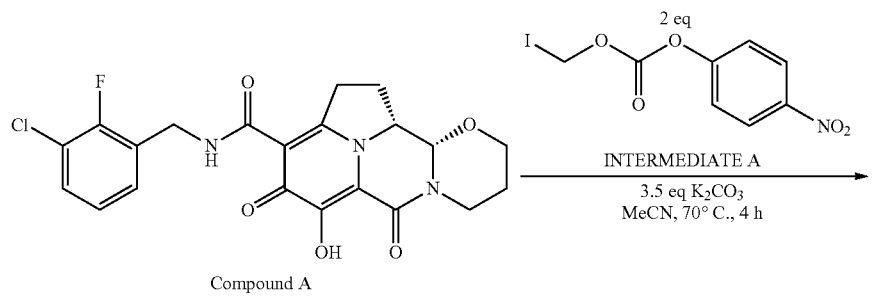

Compound A

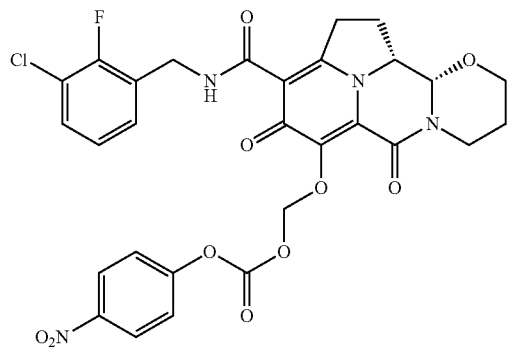

To a mixture of (11aS,11bR)-N-(3-chloro-2-fluorobenzyl)-5-hydroxy-4,6-dioxo-1,2,4,6,9,10,11a,11b-octahydro-8H-[1,3]oxazino[2',3':3,4]pyrazino[2,1,6-cd]indolizine-3-carboxamide (Compound A) (7.5 g, 16.8 mmol) and iodomethyl (4-nitrophenyl) carbonate (INTERMEDIATE A) (10.8 g, 33.5 mmol) in acetonitrile (120 mL) was added potassium carbonate (8.0 g, 57.8 mmol). The resulting mixture was stirred at 80° C. for 4 hours. The reaction mixture was cooled to ambient temperature, diluted with DCM (120 mL), and stirred at the same temperature for 20 minutes. The mixture was filtered washing with DCM (100 mL), and the filtrate was concentrated. The residue was taken back up in DCM (20 mL) and purified directly by flash chromatography (330 g RediSep Rf Gold; 0-10% MeOH in DCM in 35 minutes; CombiFlash Rf system; DP elutes ~4% MeOH). Pure fractions were combined and concentrated to afford (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (4-nitrophenyl) carbonate. LRMS (M+H)⁺: 643.3.

Step 2

(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (2-(2-methoxyethoxy)ethyl) carbonate

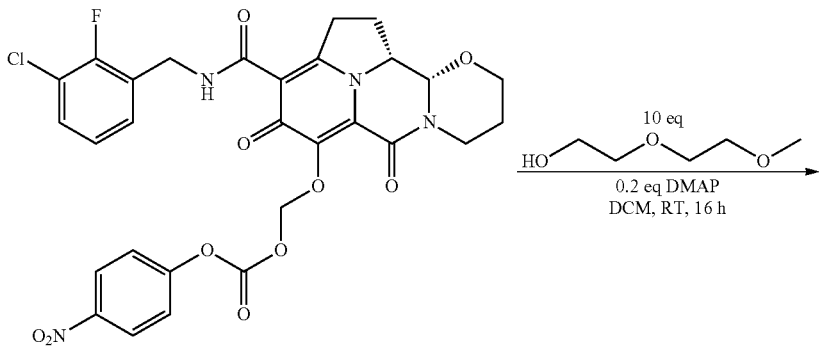

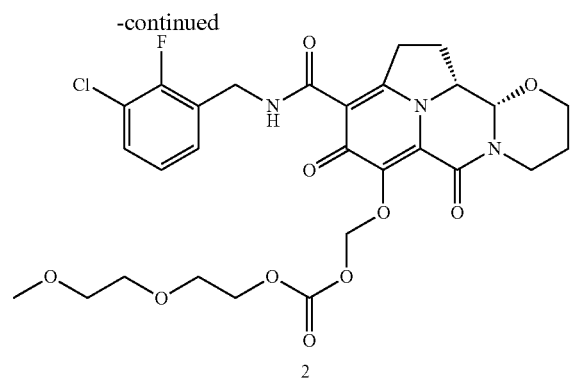

2

To a solution of (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (4-nitrophenyl) carbonate (6.5 g, 10.1 mmol) in DCM (25.3 mL) was added 2-(2-methoxyethoxy)ethan-1-ol (11.9 mL, 101 mmol) followed by DMAP (0.25 g, 2.0 mmol). The resulting mixture was stirred at room temperature overnight. The reaction mixture was purified directly by flash chromatography (330 g RediSep Rf Gold; 30-100% 3:1 EtOAc/EtOH blend in hexanes over 50 minutes; CombiFlash Rf system). Some parent Compound A co-elutes with desired product 2. Fractions containing compound 2 were combined and concentrated. The residue was dissolved in DMSO and re-purified by preparative reverse phase chromatography (Waters XBridge™ 5 micron OBD™ 30×250 mm C18 column; 200-275 mg per injection; 20-80% MeCN/water with 0.1% TFA modifier over 27 minutes). Pure fractions were neutralized with a saturated solution of aqueous sodium bicarbonate, extracted with DCM and concentrated to afford (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (2-(2-methoxyethoxy)ethyl) carbonate (Example 2). The material was then crystallized from 1:1 heptane/isopropyl acetate (300 mg/mL). 1H NMR (500 MHz, Chloroform-d) δ 10.87 (t, J=5.8 Hz, 1H), 7.26 (d, J=7.7 Hz, 2H), 7.03 (t, J=7.9 Hz, 1H), 5.85 (q, J=6.5 Hz, 2H), 4.96 (d, J=3.3 Hz, 1H), 4.76 (dd, J=13.1, 4.3 Hz, 1H), 4.59-4.70 (m, 2H), 4.52 (ddd, J=10.7, 7.0, 3.2 Hz, 1H), 4.39-4.28 (m, 2H), 4.21 (dd, J=11.6, 4.6 Hz, 1H), 4.10 (dd, J=19.1, 9.1 Hz, 1H), 3.93 (td, J=12.4, 2.2 Hz, 1H), 3.74 (t, J=4.9 Hz, 2H), 3.66-3.61 (m, 2H), 3.53 (dd, J=5.5, 3.6 Hz, 2H), 3.37 (s, 3H), 3.33-3.41 (m, 1H), 3.16-3.06 (m, 1H), 2.27-2.43 (m, 2H), 2.02 (m, 1H), 1.55 (d, J=13.7 Hz, 1H). LRMS (M+H)+: 624.3.

EXAMPLE 3

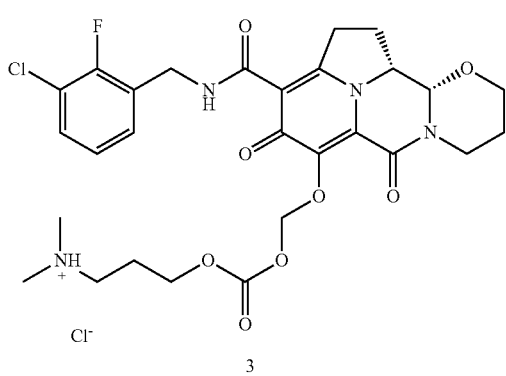

3

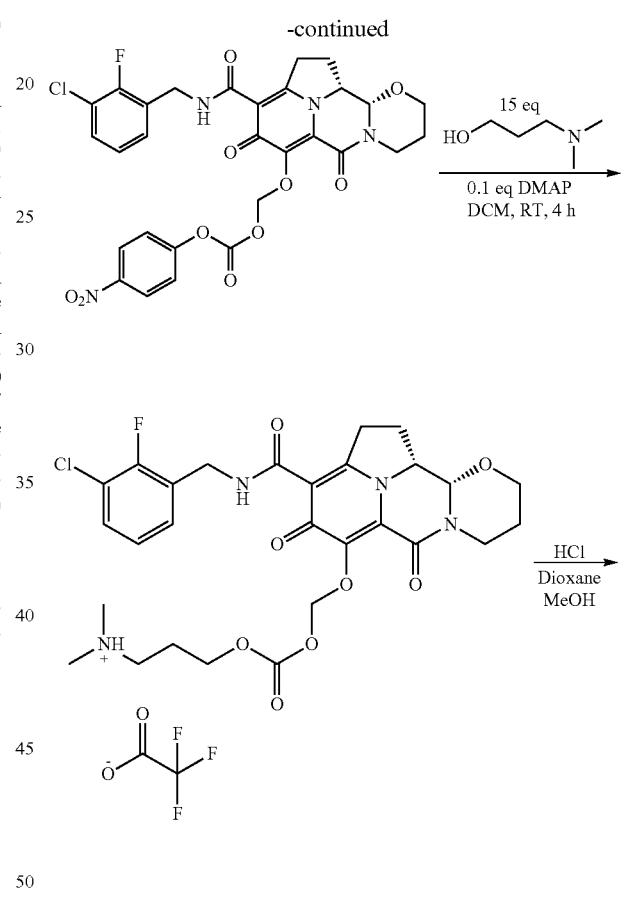

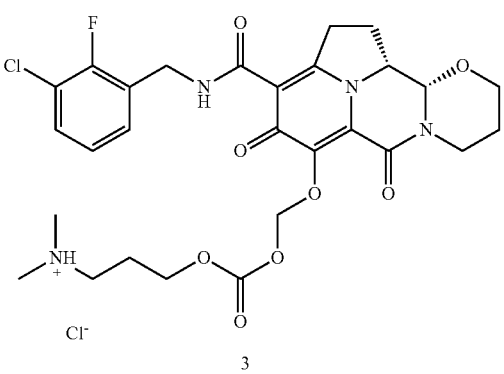

3

Step 1

(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (3-(dimethylamino)propyl) carbonate 2,2,2-trifluoroacetate

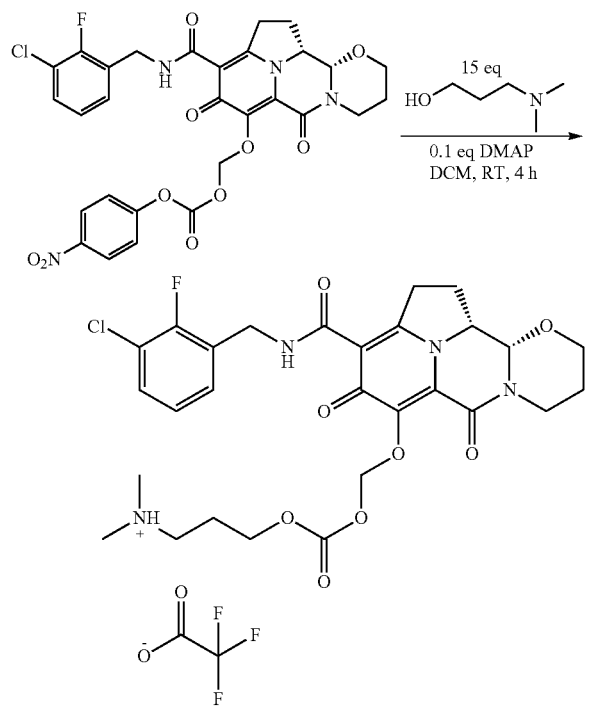

To a solution of (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (4-nitrophenyl) carbonate (1.09 g, 1.70 mmol) in DCM (8.5 mL) was added 3-(dimethylamino)propan-1-ol (2.97 mL, 25.4 mmol) followed by DMAP (21 mg, 0.17 mmol). The resulting mixture was stirred at room temperature until the reaction was complete (LCMS shows reaction nearly complete after 3 h). The mixture was concentrated, the residue dissolved in DMF, and purified directly by preparative reverse phase chromatography (Phenomenex Luna 5 micron 50×250 mm C18 column; 2 injections; 5-70% MeCN/water with 0.1% TFA modifier over 30 minutes). Pure fractions were combined and concentrated under reduced pressure (azeotroping with MeCN) to afford (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (3-(dimethylamino)propyl) carbonate 2,2,2-trifluoroacetate. LRMS (M+H)$^+$: 607.4.

Step 2

| Ex. No. | Structure | Name | Preparative Method(s) Used | LRMS (ESI) [M + 1]$^+$ |
|---|---|---|---|---|
| 4 | 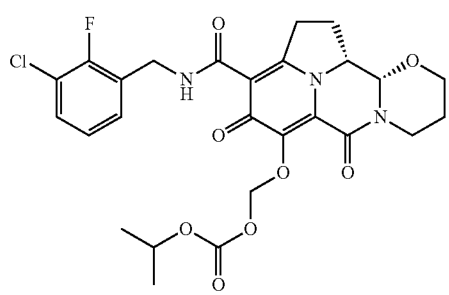 [SMILES: CC(C)OC(=O)OCOc1c2n3c(c(C(=O)NCc4cccc(Cl)c4F)c1=O)CC[C@@H]3[C@@H]1OCCCN1C2=O] | (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl isopropyl carbonate | Example 1 | 564.2 |
| 5 | 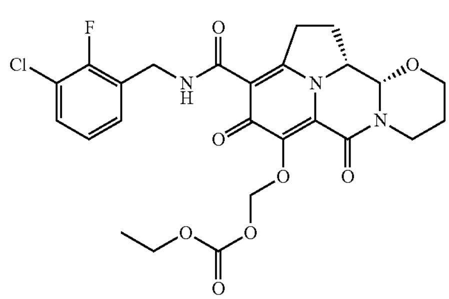 [SMILES: CCOC(=O)OCOc1c2n3c(c(C(=O)NCc4cccc(Cl)c4F)c1=O)CC[C@@H]3[C@@H]1OCCCN1C2=O] | (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl ethyl carbonate | Example 1 | 550.3 |

| Ex. No. | Structure | Name | Preparative Method(s) Used | LRMS (ESI) [M + 1]+ |
|---|---|---|---|---|
| 6 | 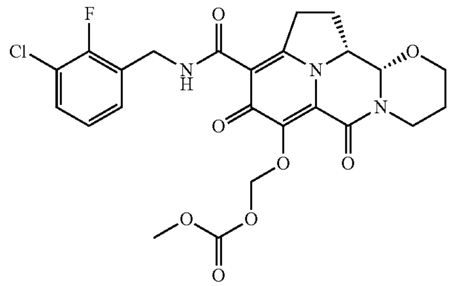 [SMILES: COC(=O)OCOc1c2n3c(c(C(=O)NCc4cccc(Cl)c4F)c1=O)CC[C@@H]3[C@@H]1OCCCN1C2=O] | (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl methyl carbonate | Example 1 | 536.3 |
| 7 | 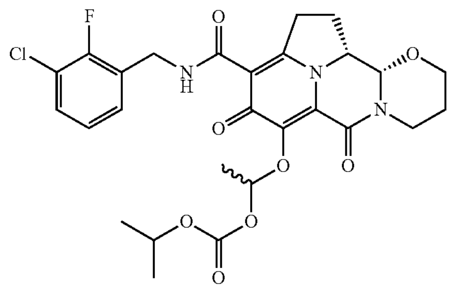 [SMILES: CC(C)OC(=O)OC(C)Oc1c2n3c(c(C(=O)NCc4cccc(Cl)c4F)c1=O)CC[C@@H]3[C@@H]1OCCCN1C2=O] | 1-(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)ethyl isopropyl carbonate | Example 1 | 578.4 |
| 8 | 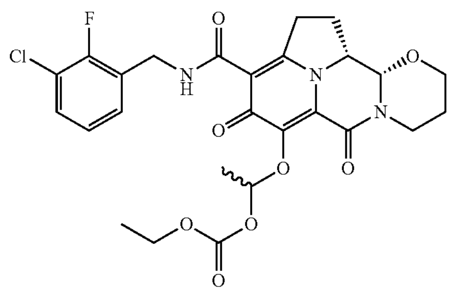 [SMILES: CCOC(=O)OC(C)Oc1c2n3c(c(C(=O)NCc4cccc(Cl)c4F)c1=O)CC[C@@H]3[C@@H]1OCCCN1C2=O] | 1-(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)ethyl ethyl carbonate | Example 1 | 564.3 |

(((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (3-(dimethylamino)propyl) carbonate hydrochloride

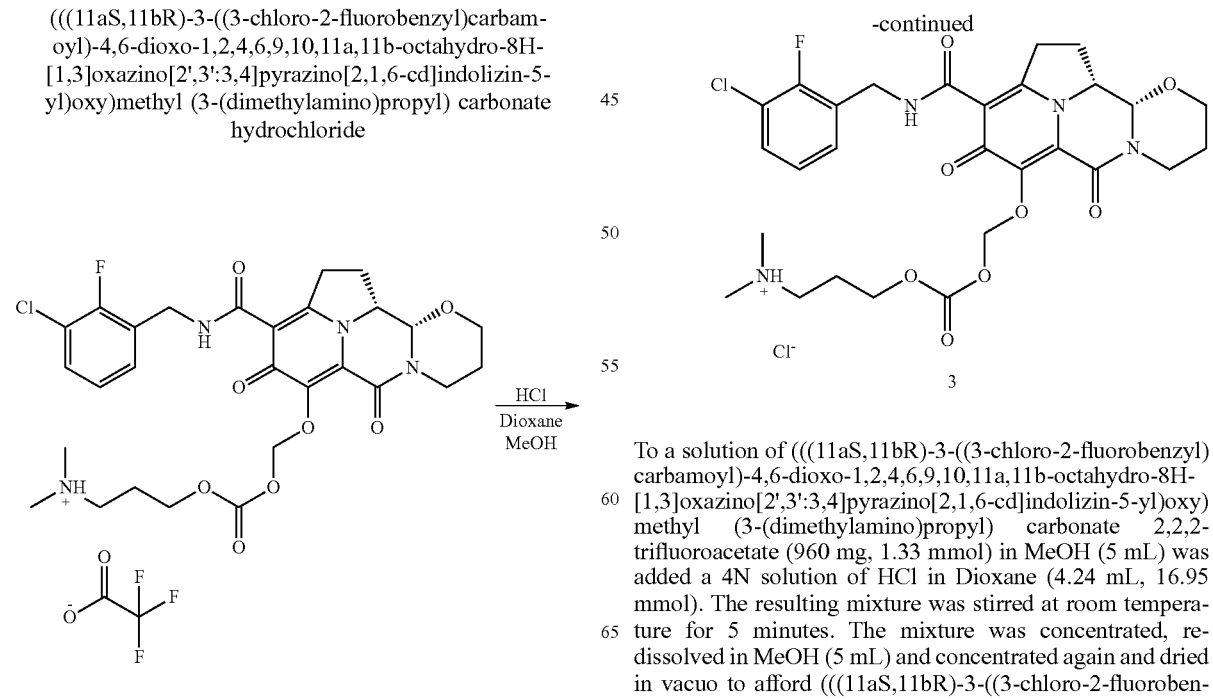

To a solution of (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy) methyl (3-(dimethylamino)propyl) carbonate 2,2,2-trifluoroacetate (960 mg, 1.33 mmol) in MeOH (5 mL) was added a 4N solution of HCl in Dioxane (4.24 mL, 16.95 mmol). The resulting mixture was stirred at room temperature for 5 minutes. The mixture was concentrated, re-dissolved in MeOH (5 mL) and concentrated again and dried in vacuo to afford (((11aS,11bR)-3-((3-chloro-2-fluorobenzyl)carbamoyl)-4,6-dioxo-1,2,4,6,9,10,11a,11b-octahydro-8H-[1,3]oxazino[2',3':3,4]pyrazino[2,1,6-cd]indolizin-5-yl)oxy)methyl (3-(dimethylamino)propyl) carbonate hydrochloride (Example 3). 1H NMR (500 MHz, Methanol-d4) 67 7.40 (t, J=7.6 Hz, 1H), 7.34 (t, J=6.8 Hz, 1H), 7.14 (t, J=7.9 Hz, 1H), 5.83 (d, J=6.8 Hz, 1H), 5.65 (d, J=6.8 Hz, 1H), 5.21 (d, J=3.3 Hz, 1H), 4.74-4.59 (m, 4H), 4.36-4.25 (m, 2H), 4.19 (dd, J=11.4, 4.6 Hz, 1H), 4.07-3.99 (m, 1H), 3.99-3.89 (m, 1H), 3.66 (s, 3H), 3.41-3.33 (m, 2H), 2.90 (d, J=15.6 Hz, 6H), 2.39-2.30 (m, 2H), 2.22-2.11 (m, 2H), 1.98-1.91 (m, 1H), 1.60 (d, J=13.4 Hz, 1H). LRMS (M+H)$^+$: 607.4.

The compounds in the following table were prepared in an analogous fashion to that described for Examples 1 above using appropriate starting materials.

Dog Pharmacokinetic Studies

Male Beagle Dogs (Marshall Farms) were used for the pharmacokinetic studies. Studies were conducted under a protocol approved by the WP-IACUC (Animal Procedure Statement #2018-600787-MAR). Following overnight-fasting, dogs were dosed orally with either Compound A at 10 mg/kg and 25 mg/kg or one of the respective prodrugs at the dose equivalent to 10 mg/kg and 25 mg/kg of Compound A formulated as a suspension in either 0.5% methylcellulose with 0.25% sodium lauryl sulfate or 10% Tween 80-5 mM HCl. Food was returned at 4 hours after dosing. Blood (0.5-mL) was drawn at pre-dose, 0.25, 0.5, 1, 2, 4, 6, 24, 48, 72, 96, and 168 hours post-dosing into EDTA-coated collection tubes containing 25 µL of 2 mM dichlorvos solution in water. The tubes were kept chilled prior to blood collection and throughout plasma separation. The plasma was separated by centrifugation (2 minutes at 10000 g). Plasma samples were immediately frozen and kept at −70° C. until analysis by LC-MS/MS.

Mean [± SD] pharmacokinetic parameters for compounds after oral administration to fasted Beagle dogs at dose equivalent to 10 mg/kg of Compound A.

| Compound Dosed | Dosing Route | Compound Measured | AUC0-168 hr (µM · hr) | Cmax (µM) |
|---|---|---|---|---|
| A | Oral | A | 6133 ± 1408 | 58 ± 18 |
| 1 | Oral | A | 6870 ± 408 | 74 ± 15 |
| 2* | Oral | A | 9633 ± 2311 | 134 ± 34 |
| 3* | Oral | A | 5369 ± 1016 | 65 ± 11 |
| 4 | Oral | A | 2282 ± 249 | 22 ± 0.8 |
| 5 | Oral | A | 2595 ± 571 | 41 ± 8.4 |
| 6 | Oral | A | 6198 ± 1436 | 48 ± 6 |
| 7 | Oral | A | — | — |
| 8 | Oral | A | — | — |

*PK data for amorphous prodrug.

Mean [± SD] pharmacokinetic parameters for compounds after oral administration to fasted Beagle dogs at dose equivalent to 25 mg/kg of Compound A.

| Compound Dosed | Dosing Route | Compound Measured | AUC0-168 hr (µM · hr) | Cmax (µM) |
|---|---|---|---|---|
| A | Oral | A | 8371 ± 386 | 79 ± 17 |
| 1 | Oral | A | 13376 ± 890 | 157 ± 19 |
| 2 | Oral | A | pending | pending |
| 3 | Oral | A | — | — |
| 4 | Oral | A | — | — |
| 5 | Oral | A | — | — |
| 6 | Oral | A | 9861 ± 968 | 103 ± 7 |
| 7 | Oral | A | — | — |
| 8 | Oral | A | — | — |

As shown above, Compounds 1 and 6, which are representative compounds of the present invention, show increase in absorption versus their metabolite, Compound A.

Treatment or Prevention of HIV Infection

The Tetracyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Tetracyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Tetracyclic Heterocycle Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Tetracyclic Heterocycle Compounds are also useful in the preparation and execution of screening assays for antiviral compounds. For example the Tetracyclic Heterocycle Compounds may be useful for identifying resistant HIV cell lines harboring mutations, which are excellent screening tools for more powerful antiviral compounds. Furthermore, the Tetracyclic Heterocycle Compounds may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Tetracyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Tetracyclic Heterocycle Compound (which may include two or more different Tetracyclic Heterocycle Compounds), or a pharmaceutically acceptable salt or prodrug thereof, and (ii) at least one additional therapeutic agent that is other than a Tetracyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tetracyclic Heterocycle Compound and an additional therapeutic agent may be present in fixed amounts (dosage amounts) in a single dosage unit (e.g., a capsule, a tablet and the like).

In one embodiment, at least one Tetracyclic Heterocycle Compound is administered during a time when the additional therapeutic agent(s) exert their prophylactic or therapeutic effect, or vice versa.

In another embodiment, at least one Tetracyclic Heterocycle Compound and the additional therapeutic agent(s) are administered in doses commonly employed when such agents are used as monotherapy for treating a viral infection.

In another embodiment, at least one Tetracyclic Heterocycle Compound and the additional therapeutic agent(s) are administered in doses lower than the doses commonly employed when such agents are used as monotherapy for treating a viral infection.

In still another embodiment, at least one Tetracyclic Heterocycle Compound and the additional therapeutic agent(s) act synergistically and are administered in doses lower than the doses commonly employed when such agents are used as monotherapy for treating a viral infection.

In one embodiment, at least one Tetracyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Tetracyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tetracyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
|---|---|
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| cabotegravir | Cabenuva ®, Vocabria ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | Pifeltro ® |
| doravirine + lamivudine + tenofovir DF | Delstrigo ® |
| efavirenz, EFV | Sustiva ®, Stocrin ® |
| efavirenz + emtricitabine + tenofovir DF | Atripla ® |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| islatravir (EFdA, 4'-ethynyl-2-fluoro-2'-deoxyadenosine) | |
| lamivudine, 3TC | Epivir ® |
| lamivudine + zidovudine | Combivir ® |
| lenacapavir | |
| Lopinavir | |
| lopinavir + ritonavir | Kaletra ® |
| maraviroc | Selzentry ® |
| nelfinavir | Viracept ® |
| nevirapine, NVP | Viramune ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine, doravirine, EFdA and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with islatravir.

In another embodiment, the compound of formula (I) is used in combination with emtricitabine and tenofovir.

In still another embodiment, the compound of formula (I) is used in combination doravirine.

In still another embodiment, the compound of formula (I) is used in combination doravirine, lamivudine and tenofovir DF.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir, islatravir, doravirine and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir, islatravir, doravirine and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tetracyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Tetracyclic Heterocycle Compounds may be administered as a component of a composition that comprises a pharmaceutically acceptable carrier or vehicle. The present invention provides pharmaceutical compositions comprising an effective amount of at least one Tetracyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate-controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tetracyclic Heterocycle Compounds are administered orally.

In another embodiment, the one or more Tetracyclic Heterocycle Compounds are administered intravenously.

In one embodiment, a pharmaceutical preparation comprising at least one Tetracyclic Heterocycle Compound is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Tetracyclic Heterocycle Compound(s) by weight or volume. In various embodiments, the present compositions can contain, in one embodiment, from about 1% to about 70% or from about 5% to about 60% of the Tetracyclic Heterocycle Compound(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Tetracyclic Heterocycle Compounds may be administered at varying frequencies. In one embodiment, a unit dosage of a Tetracyclic Heterocycle Compound may be administered once daily. In another embodiment, a unit dosage of a Tetracyclic Heterocycle Compound may be administered twice weekly. In another embodiment, a unit dosage of a Tetracyclic Heterocycle Compound may be administered once weekly. In still another embodiment, a unit dosage of a Tetracyclic Heterocycle Compound may be administered once biweekly. In another embodiment, a unit dosage of a Tetracyclic Heterocycle Compound may be administered once monthly. In yet another embodiment, a unit dosage of a Tetracyclic Heterocycle Compound may be administered once bimonthly. In another embodiment, a unit dosage of a Tetracyclic Heterocycle Compound may be administered once every 3 months. In a further embodiment, a unit dosage of a Tetracyclic Heterocycle Compound may be administered once every 6 months. In another embodiment, a unit dosage of a Tetracyclic Heterocycle Compound may be administered once yearly.

The amount and frequency of administration of the Tetracyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Tetracyclic Heterocycle Compound, or a pharmaceutically acceptable salt or prodrug of said compound and a pharmaceutically acceptable carrier, vehicle or diluent.

In another aspect the present invention provides a kit comprising an amount of at least one Tetracyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Tetracyclic Heterocycle Compounds and the one or more additional therapeutic agents are provided in the same container. In one embodiment, the one or more Tetracyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula (I):

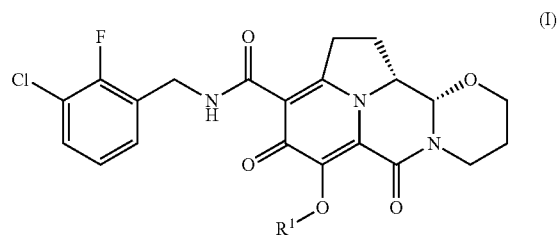

wherein:

R¹ is CHR²—O—C(O)—Y—R³, C(O)—C₁-C₁₀ alkyl, CHR²—O—P(O)(OH)₂ or

[structure: methyl dioxolone]

Y is a bond or —O—;
R² is hydrogen or C₁-C₆ alkyl;
R³ is selected from the group consisting of C₁-C₆ alkyl, (CH₂)ₓ—O—C₁-C₆ alkyl, and (CH₂)ₓ—NR⁴R⁵, wherein said C₁-C₆ alkyl group can be optionally substituted with one to three groups independently selected from the group consisting of halo, hydroxy, methoxy and ethoxy;
R⁴ is hydrogen or C₁-C₆ alkyl;
R⁵ is hydrogen or C₁-C₆ alkyl;
x is an integer from one to four;
or a pharmaceutically acceptable salt thereof.

2. The compound of claim 1, wherein Y is O, or a pharmaceutically acceptable salt thereof.

3. The compound of claim 2 wherein R² is hydrogen or methyl; or a pharmaceutically acceptable salt thereof.

4. The compound of claim 3 wherein R³ is C₁-C₆ alkyl, which is optionally substituted with one to three groups independently selected from the group consisting of halo, hydroxy, methoxy and ethoxy; or a pharmaceutically acceptable salt thereof.

5. The compound of claim 4 wherein R³ is (CH₂)ₓ—O—C₁-C₆ alkyl and x is two; or a pharmaceutically acceptable salt thereof.

6. The compound of claim 5 wherein R³ is (CH₂)ₓ—NR⁴R⁵; or a pharmaceutically acceptable salt thereof.

7. The compound of claim 6 wherein R⁴ is methyl and R⁵ is methyl; or a pharmaceutically acceptable salt thereof.

8. The compound of claim 7 wherein R¹ is selected from:

[structures of R¹ groups]

or a pharmaceutically acceptable salt thereof.

9. The compound of claim 8 wherein R¹ is

[structure]

or a pharmaceutically acceptable salt thereof.

10. The compound of claim 1 having the structure

[structure of final compound]

-continued

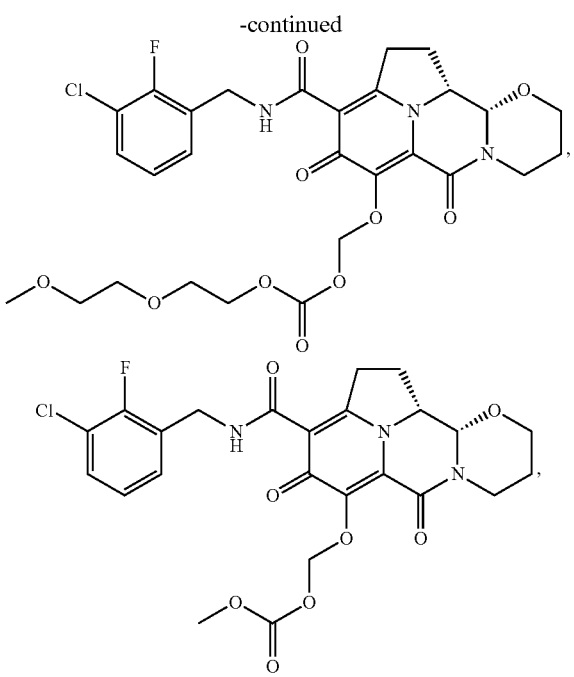

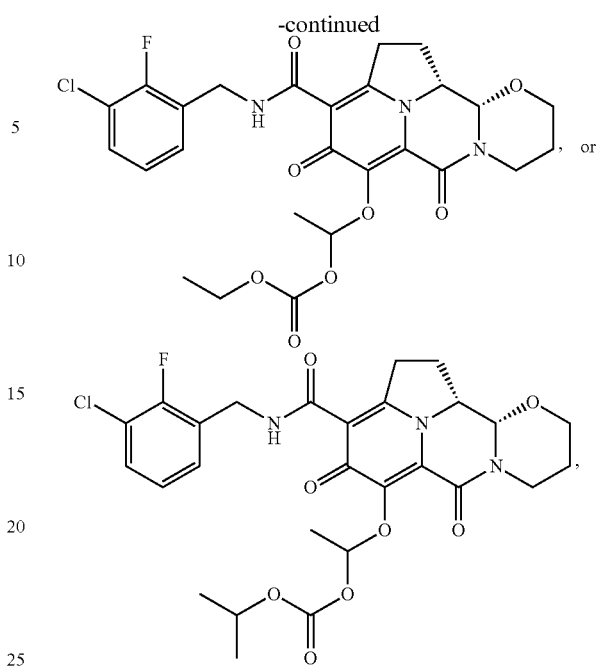

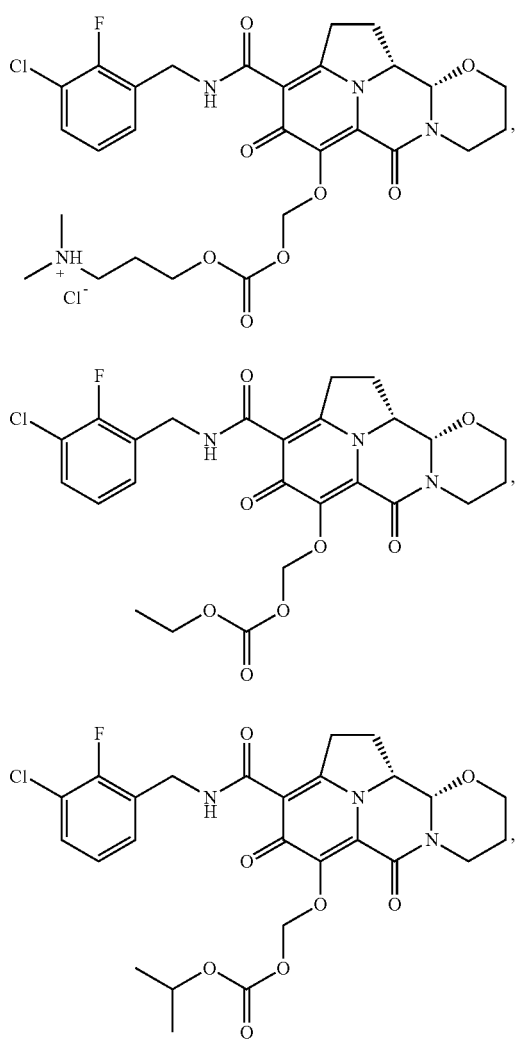

or a pharmaceutically acceptable salt thereof.

11. A pharmaceutical composition comprising an effective amount of the compound according to claim 1, or a pharmaceutically acceptable salt thereof, and a pharmaceutically acceptable carrier.

12. The composition of claim 11, further comprising one or more additional therapeutic agents selected from the group consisting of raltegravir, lamivudine, abacavir, ritonavir, dolutegravir, darunavir, atazanavir, emtricitabine, tenofovir, elvitegravir, rilpivirine, lopinavir, doravirine, lenacapavir and islatravir.

13. The pharmaceutical composition of claim 11, wherein the composition is in the form of a tablet.

14. The pharmaceutical composition of claim 11, wherein the composition is in the form of a capsule.

15. A method for the inhibition of HIV integrase in a subject in need thereof which comprises administering to the subject an effective amount of the compound according to claim 1, or a pharmaceutically acceptable salt thereof.

16. A method for the treatment of infection by HIV or for the treatment or delay in the onset or progression of AIDS in a subject in need thereof, which comprises administering to the subject an effective amount of the compound according to claim 1, or a pharmaceutically acceptable salt thereof.

17. The method of claim 16, further comprising administering to the subject one or more additional therapeutic agents selected from the group consisting of raltegravir, lamivudine, abacavir, ritonavir, dolutegravir, darunavir, atazanavir, emtricitabine, tenofovir, elvitegravir, rilpivirine, lopinavir, doravirine, lenacapavir and islatravir wherein the amounts administered of the compound of claim 1 and the one or more additional therapeutic agents, are together effective to treat infection by HIV or to treat, prevent or delay the onset or progression of AIDS.

18. The method of claim 16, wherein an effective amount of the compound is administered to the subject once daily.

19. The method of claim 16, wherein an effective amount of the compound is administered to the subject in two divided doses over a 24-hour period.

* * * * *